(12) United States Patent
Nifantiev et al.

(10) Patent No.: US 9,216,166 B2
(45) Date of Patent: Dec. 22, 2015

(54) ANTI-MICROBIAL PHOTODYNAMIC THERAPY

(75) Inventors: Nikolay E. Nifantiev, Moscow (RU); Burkhard Gitter, Jena (DE); Dmitri V. Yashunsky, Moscow (RU)

(73) Assignee: Biolitec Pharma Marketing, Ltd, Labuan (MY)

( * ) Notice: Subject to any disclaimer, the term of this patent is extended or adjusted under 35 U.S.C. 154(b) by 967 days.

(21) Appl. No.: 12/375,241

(22) PCT Filed: Jul. 27, 2007

(86) PCT No.: PCT/US2007/016951
§ 371 (c)(1),
(2), (4) Date: Jan. 27, 2009

(87) PCT Pub. No.: WO2009/014524
PCT Pub. Date: Jan. 29, 2009

(65) Prior Publication Data
US 2009/0326434 A1    Dec. 31, 2009

Related U.S. Application Data

(63) Continuation of application No. 11/880,974, filed on Jul. 25, 2007, now abandoned.

(60) Provisional application No. 60/833,836, filed on Jul. 27, 2006.

(51) Int. Cl.
*A61K 31/407* (2006.01)
*A61K 47/48* (2006.01)
*A61K 41/00* (2006.01)

(52) U.S. Cl.
CPC ........... *A61K 31/407* (2013.01); *A61K 41/0071* (2013.01); *A61K 47/48246* (2013.01)

(58) Field of Classification Search
CPC .................................................... A61K 31/407
See application file for complete search history.

(56) References Cited

U.S. PATENT DOCUMENTS

| | | | |
|---|---|---|---|
| 5,466,681 A | 11/1995 | Krivan et al. | |
| 6,462,070 B1 | 10/2002 | Hasan et al. | |
| 6,573,258 B2 | 6/2003 | Bommer et al. | |
| 6,777,402 B2 * | 8/2004 | Nifantiev et al. | 514/183 |
| 6,977,075 B2 | 12/2005 | Hasan et al. | |
| 7,770,437 B2 * | 8/2010 | Frederix et al. | 73/61.41 |
| 2002/0183245 A1 * | 12/2002 | Hasan et al. | 514/6 |

FOREIGN PATENT DOCUMENTS

| | | | | |
|---|---|---|---|---|
| WO | 95/03327 | * | 2/1995 | C07K 14/00 |
| WO | 96/38163 | * | 12/1996 | A61K 38/04 |
| WO | 01/27261 | * | 4/2001 | C12N 15/11 |
| WO | WO 2004/085387 | * | 10/2004 | |

OTHER PUBLICATIONS

Baek et al., 2000, Design and Synthesis of Novel Glycopolythiophene Assemblies for Colorimetric Detection of Influenza Virus and *E. coli*, 11: 777-788.*
Roberts et al., 2002, Chemistry for peptide and protein PEGylation, Advanced Drug Delivery Reviews, 54: 459-476.*
Postigo et al., 2006, Photosensitization of skin fibroblasts and HeLa cells by three chlorin derivatives: Role of chemical structure and delivery vehicle, Biochimica et Biophysica Acta, 1758: 583-596.*
Li et al., 2003, Synthesis, Comparative Photosensitizing Efficacy, Human Serum Albumin (Site II) Binding Ability, and Intracellular Localization Characteristics of Novel Benzobacteriochlorins Derived from vic-Dihydroxybacteriochlorins, J Med Chem, 46: 5349-5359.*

* cited by examiner

*Primary Examiner* — Amber D Steele
(74) *Attorney, Agent, or Firm* — BJ Associates; Bolesh J Skutnik

(57) ABSTRACT

Antimicrobial molecular conjugates for the treatment and prevention of infectious diseases caused by pathogenic microorganisms in human and animals are provided. The key to these conjugates is a special spacer connecting at least one photosensitizer to a microorganism receptor (vector) which in turn binds selectively to the surface of a microorganism bringing about photo-destruction upon irradiation. Spacers having hydrophilic structure such as ethylene glycol units and amino carboxyl end capped ethylene glycol units must be used for linking the vector to the photosensitizer. In a preferred embodiment a spacer would have at least 3 ethylene glycol units and be end capped with a carboxyl group on one end and a amino group at the other end. The present invention effectively works to combat bacterial infection in the real patient-related environments where blood, serum and other body fluids are always present or at least nearby. Spacers of selected length and structure, in preferred embodiments, are used for linking the vector to the photosensitizer. These conjugate are found to be very effective in combating bacterial infection in the real patient-related environments where blood, serum and other body fluids are always present or a least nearby. A method of use is also provided.

7 Claims, 6 Drawing Sheets

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide

<400> SEQUENCE: 1

Lys Phe Phe Lys Phe Phe Lys Phe Phe Lys
1               5                   10
```

ANTI-MICROBIAL PHOTODYNAMIC THERAPY

DOMESTIC PRIORITY UNDER 35 USC 119(e)

This application is a national stage application of PCT/US2007/016951, filed Jul. 27, 2007, which is a continuation of U.S. application Ser. No. 11/880,974, filed Jul. 25, 2007, now abandoned, and claims the benefit of U.S. Provisional Application Ser. No. 60/833,836 filed Jul. 27, 2006. Each of these applications is incorporated by reference in entirety herein.

In compliance with 37 C.F.R. §1.52(e)(5), a Computer Readable Form of the Sequence Listing was filed in electronic form, file name: BJA409A2_SEQList_ST25.txt; size 1 KB; created on: Sep. 9, 2011; using Patent-In 3.5, and Checker 4.4.0, which is hereby incorporated herein by reference in its entirety.

BACKGROUND OF THE INVENTION

1. Field of the Invention

The present invention relates generally to photodynamic therapy, and particularly to molecular conjugates for the treatment and prevention of microbial infectious diseases in human and animals. A molecular conjugate of the present invention comprises a special spacer to connect at least one photosensitizer, with a vector.

2. Invention Disclosure Statement

Photodynamic therapy (PDT) is a relatively new treating modality for cancers and other diseases. Photosensitizers are administered systemically, locally or topically and accumulate in the tumor or other lesion; illuminating the area with light energy to excite the sensitizer, which, in the presence of oxygen, produces cytotoxic effects in the cells. Another important application of PDT is the treatment of infectious diseases caused by pathogenic microorganisms.

Antimicrobial photodynamic therapy is very promising method for combating bacterial infection even for resistant strains. Fortunately, no resistance to photodynamic destruction has been reported to be acquired by bacteria nor is it likely since the 'killing species' is oxygen. Bacterial cells treated with photosensitizers were shown to be successfully killed by photo illumination. None of the known photosensitizers and photosensitizer conjugates is effective against all bacteria, as activity mainly depends on their chemical structure. Effectiveness of the photosensitizer also depends on the bacterial cell wall as it becomes the limiting factor for the sensitizer penetration. In the case of Gram-negative bacteria their double-layer outer membrane structure is the main obstacle.

Cell structures of Gram-positive and Gram-negative bacteria are different and it is differentiated by their Gram staining characteristics. The Gram-positive cell wall is characterized by the presence of a very thick layer of peptidoglycan. Embedded in the Gram-positive cell wall are polyalcohols called teichoic acids, some of which are lipid linked to form lipoteichoic acids. Teichoic acids give the Gram-positive cell wall an overall negative charge due to the presence of phosphodiester bonds between teichoic acid monomers. While Gram-negative bacterial cell wall contains a thin peptidoglycan layer adjacent to cytoplasmic membrane, in addition to this it has another outer membrane composed by phospholipids and lipopolysaccharides. The highly charged nature of lipopolysaccharides confers an overall negative charge to Gram-negative bacterial cell wall. The chemical structure of the outer membrane lipopolysaccharides is often unique to specific bacterial strains (i.e. sub-species) and is responsible for many of the antigenic properties of these strains.

One of the major problems for the use of anti-microbial PDT is a blocking action of the components of the blood whose presence decreases the activity of photosensitizers. This effect is exemplified on FIG. 1 demonstrating photodynamic inactivation of *Staphylococcus aureus* (Gram-positive bacterium), *Pseudomonas aeruginosa* and *Escherichia coli* with known photosensitiser (Gram-negative bacterium) Safranin O which exists in two tautomeric forms.

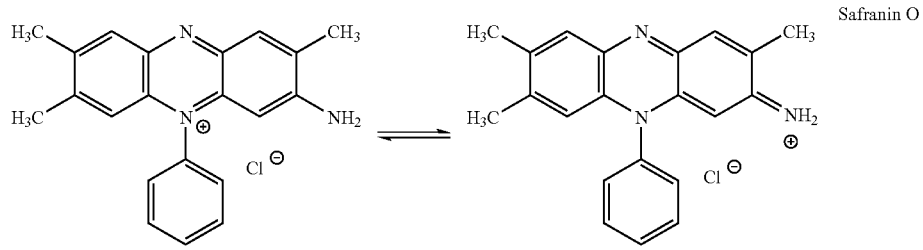 [SMILES: Cc1cc2nc3cc(C)c(N)cc3[n+](-c3ccccc3)c2cc1C ; [Cl-] ; Cc1cc2nc3cc(C)c(=[NH2+])cc-3n(-c3ccccc3)c2cc1C ; [Cl-]]

Safranin O

As seeing from FIG. 1 Safranin O exhibits high bactericidal photodynamic activity in PBS buffer that decreased remarkably when of the blood serum or blood is added. Particularly, the addition of even 10% of horse serum or human plasma or even whole blood could practically block the photodynamic activity of this sensitizer against *Pseudomonas aeruginosa*. The antibacterial effect strongly depends on the kind of bacterial cells. While Gram-positive cells of *Staphylococcus aureus* could be killed sufficiently. Gram-negative cells of *Pseudomonas aeruginosa* or *Escherichia coli* are more resistant to killing by PDT.

One of the prospective approaches to increase the specificity of photosensitizers and the effectiveness of PDT against bacterial infection is to conjugate a photosensitizer with a ligand-vector, which specifically binds to receptors on the surface of a target cell, in the prior art different methods have been used to effectively target the pathogen or the infected cells.

In U.S. Pat. No. 6,977,075 by Hasan et al., discloses a method of killing intracellular pathogen using antibiotics and PDT. The intracellular pathogens are targeted using conjugated photosensitizers. Targeting moiety used are molecules or a macromolecular structure that target macrophages or that interacts with a pathogen. Effectiveness of the conjugate against Gram-negative, and, in complex environment is not disclosed.

In U.S. Pat. No. 6,573,258 by Bommer, et al., he describes positively charged porphyrins which can effectively target both Gram-positive and Gram-negative bacteria when present at much lower concentrations and at much shorter irradiation times. The novel porphyrins have one hydrophobic tail consisting of at least one hydrocarbon chain of between 6 and 22 carbon in length. Bacterial targeting depends upon the carbon chain length and is not very effective.

In U.S. Pat. No. 6,462,070 by Hasan, et al., discloses a photosensitizer conjugated to polylysine which is linked to a histatin targeting moiety to treat disorder of the oral cavity infected by microorganism. Different types of targeting moiety disclosed here include non-pair member polypeptide, small anti-microbial peptide, low density lipoprotein etc. Effectiveness of the conjugates on the complex environment like blood, serum etc. is not disclosed in here.

U.S. Pat. No. 5,466,681 describes a variety of conjugates useful for the treatment of infectious diseases due to pathogenic microorganisms. The conjugates comprise at least one agent coupled to a microorganism receptor—a carbohydrate vector; said vector is able to bind selectively to a microorganism. The agent is a penicillin antibiotic and said vector is an asialoganglioside or another carbohydrate chain. The conjugates are administered for the treatment of bacterial infections, particularly, caused by *Streptococcus pneumoniae* and by *Helicobacter pylori*.

A wide variety of natural and synthetic molecules recognized by target cells could be used as vectors. The use of oligopeptides and big protein molecules, including lectins, growth factors and especially antibodies to specific tumor cell antigens are known in the art. The '681 patent discloses a conjugate comprising at least one agent that is an anti-infective coupled to a microorganism receptor. Agents such as antibiotics, synthetic drugs and steroids are mentioned. Since photosensitizers do not themselves interact with microbes, they are not considered agents as described in the '681 patent and were not disclosed therein.

"Polycationic photosensitizer conjugates: effects of chain length and Gram classification on the photodynamic inactivation of bacteria", Michael R. Hamblin, David A. O'Donnell, Naveen Murthy, Krishanan Rajagopalan. Norman Michaud, Margaret E. Sherwood and Tayyaba Hasan, Journal of Antimicrobial Chemotherapy 49 (2002) pp. 941-951; In this publication the relationship between the size of the polyLysine chain and its effectiveness for mediating the killing of Gram-negative and Gram-positive bacteria. The result of the present study implies that, in the case of polycationic photosensitizer conjugates, it is necessary for the photosensitizer to gain access through the outer membrane permeability barrier. The efficiency with which this occurs depends on the size of the polycationic chain. Conjugates with 8, 37 lysines and free chlorin $e_6$ used in the study were found to be effective against bacterial infection but only 37-lysine conjugate killed the bacteria.

Anti-microbial PDT is effective mostly against Gram-positive bacteria when compared to Gram-negative bacteria. Hence there is an urgent requirement to develop a molecular conjugate which can actively target both Gram-positive and Gram-negative bacteria. Also needs to work in in vivo condition where typically or often blood and other body fluids are present, to use with patients directly to help protect them from deleterious microorganisms.

OBJECTIVES AND BRIEF SUMMARY OF THE INVENTION

It is an objective of the present invention to provide a molecular conjugate for targeting pathogenic microorganism causing infectious diseases.

It is another objective of the present invention to develop photodynamic method for inactivation/reduction of bacteria (both Gram-positive and Gram-negative) in complex environment like blood, serum and saliva.

It is still another objective of the present invention to use a special spacer to link a vector, which targets selected microorganisms specifically.

It is also yet another objective of the present invention to provide a hydrophilic spacer linking a hydrophobic photosensitizer to a microorganism targeting vector.

Briefly stated, the present invention provides antimicrobial molecular conjugates for the treatment and prevention of infectious diseases caused by pathogenic microorganisms in human and animals. The key to these conjugates is a special spacer connecting at least one photosensitizer to a microorganism receptor (vector) which in turn binds selectively to the surface of a microorganism bringing about photo-destruction upon irradiation. Spacers having hydrophilic structure such as ethylene glycol units and amino carboxyl end capped ethylene glycol units must be used for linking the vector to the photosensitizer. In a preferred embodiment a spacer would have at least 3 ethylene glycol units, with a maximum of 45 atoms in the skeletal chain, and be end capped with a carboxyl group on one end and a amino group at the other end. The present invention effectively works to combat bacterial infection in the real patient-related environments where blood, serum and other body fluids are always present or at least nearby. Spacers of selected length and structure, in preferred embodiments, are used for linking the vector to the photosensitizer. These conjugate are found to be very effective in combating bacterial infection in the real patient-related environments where blood, serum and other body fluids are always present or a least nearby. A method of use is also provided.

The above and other objects, features and advantages of the present invention will become apparent from the following description read in conjunction with the accompanying drawings.

DETAILED DESCRIPTION OF PREFERRED EMBODIMENTS

Figure 1A:
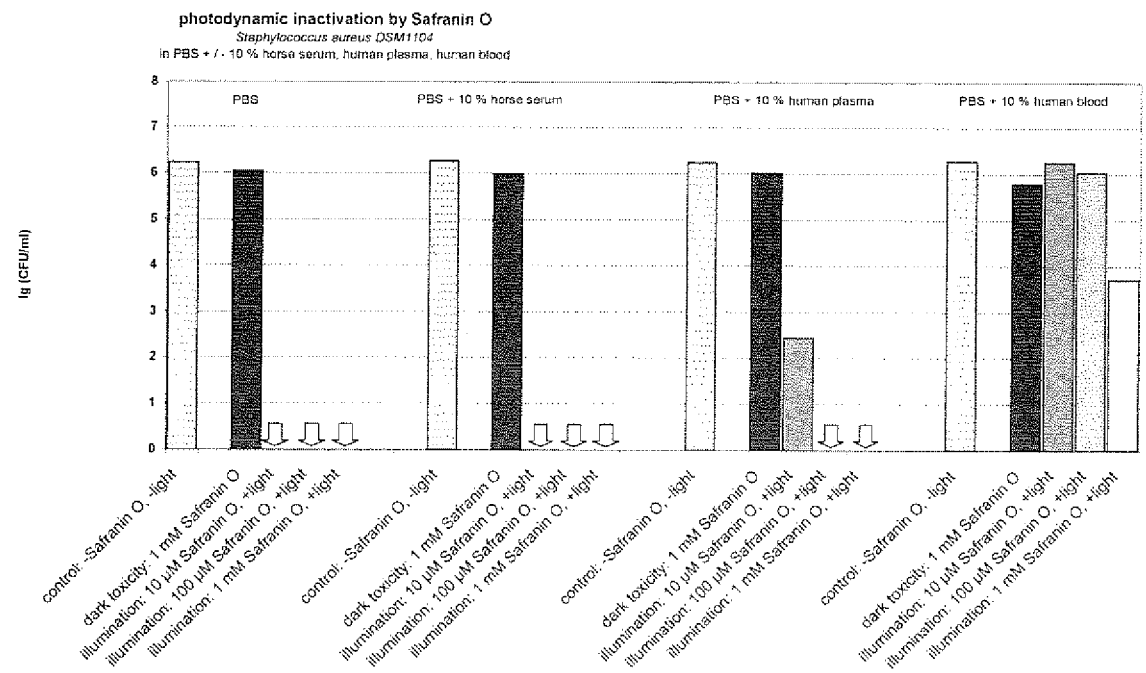
FIG. 1, Graph showing photodynamic inactivation of *Staphylococcus aureus* DSM1104 (FIG. 1A), *Pseudomonas aeruginosa* DSM1 117 (FIG. 1B), and *Escherichia coli* DSM8698 (FIG. 1C) by treatment with Safranin O as a photo sensitizer.
Figure 1B:
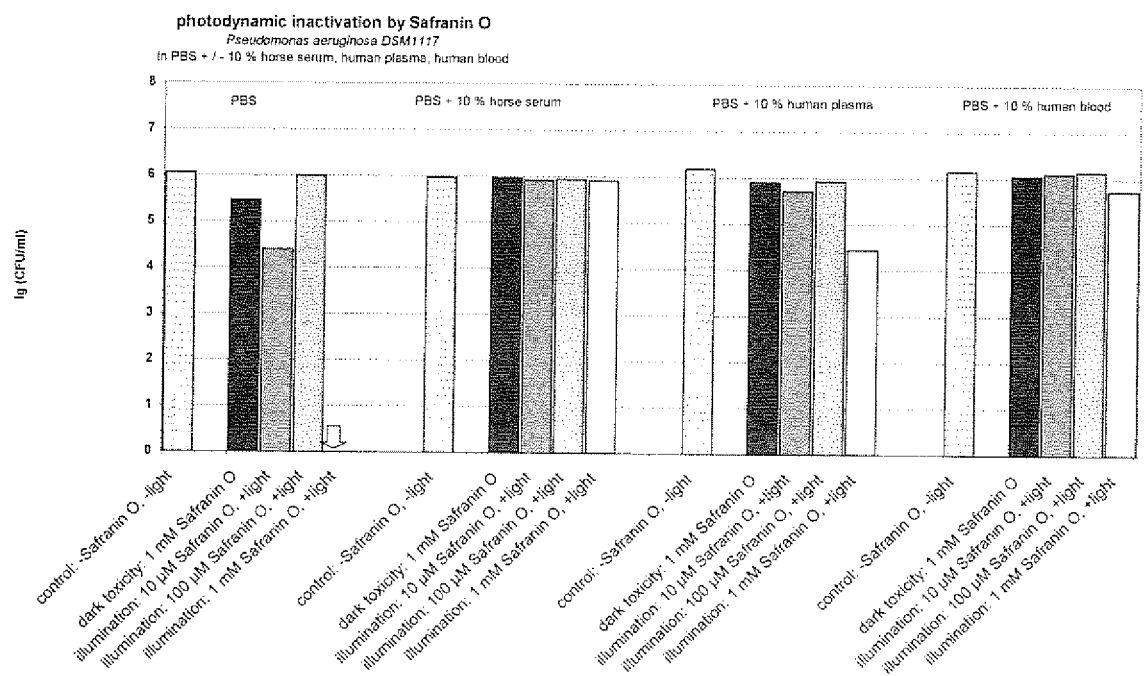
Figure 1C:
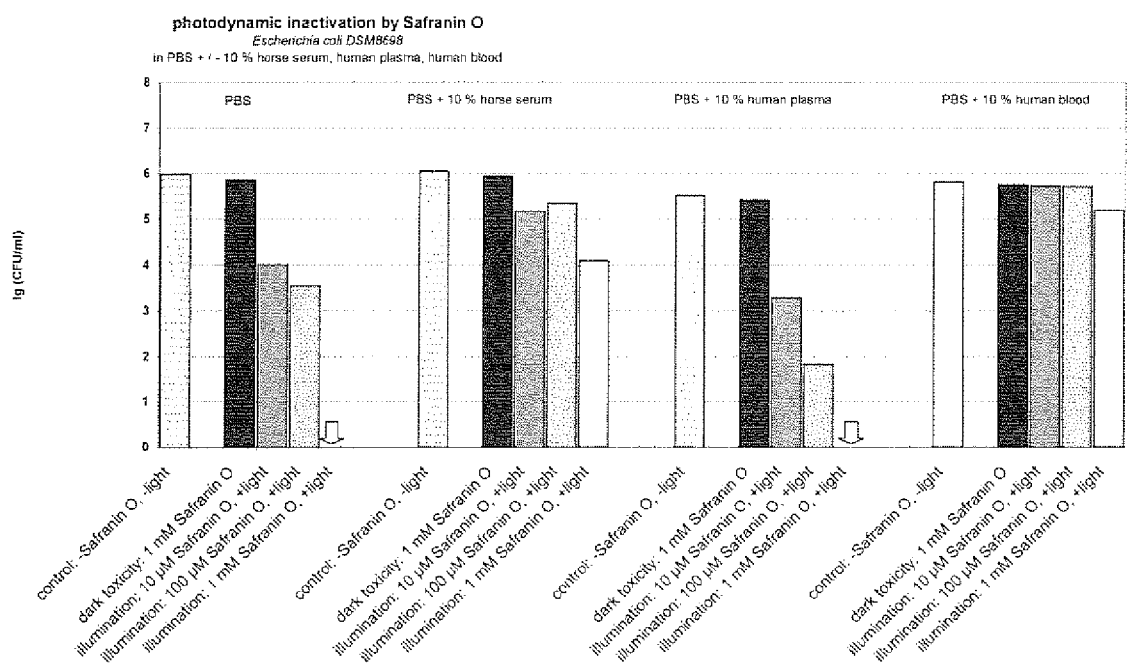

In the present invention a photodynamic method for inactivation/reduction of bacteria in complex environment is disclosed. Combating bacterial infection in the complex media present in vivo, like serum, plasma or blood is most difficult part as seen in the prior art. Here in this invention antimicrobial photodynamic therapy is used to target pathogenic microorganisms using conjugated photosensitizers to treat various infectious diseases and also to induce photodestruction in the complex media normally found in vivo for real patients. In this present invention a molecular conjugate disclosed is designed to target both Gram-positive and Gram-negative bacteria even their resistant strains. The molecular conjugate comprises of one photosensitizer linked to a vector (antimicrobial peptide) via a specially selected spacer molecule whose presence in the structure of a conjugate between vector and photosensitizer plays critical influence on conjugate activity as well as the structure of the spacer.

In the present invention antimicrobial peptides of varying length and structure are used as vector which can improve the targeting ability of the photosensitizer and also facilitate the membrane permeability in the bacterial cell wall because of the ability of such peptide sequences to associate with microbial membranes. The peptide vectors used in present invention include the oligopeptide fragments of eel 1-permeabilizing peptides or derived from lipopolysaccharide binding proteins but are not limited thereby. The selectivity of targeting moiety permits increased targeting of photosensitizer by using the conjugate of the present invention thus minimizing the dosage and adverse side-effect.

Applicability of conjugate between vector and photosensitizer of present invention and the importance of spacer moiety is demonstrated by us on the examples of conjugates 3a-e where the compound 3a has no spacer in its structure, and other compounds (3b-e) have the spacer with varied length and hydrophobicity. Preparation of products 3a-e from meso pyropheophorbide-a (1) is demonstrated in the Examples 1-6. Preparation of conjugate 3a (no spacer in the structure) comprises direct attachment of vector moiety to the compound 1 by conventional solid and liquid phase methods know in the art and exemplified below.

Synthesis of spacer-armed conjugates 3b-e includes first attachment of the appropriate spacer to the compound 1 and further coupling with the vector by conventional solid and liquid phase methods know in the art and exemplified below.

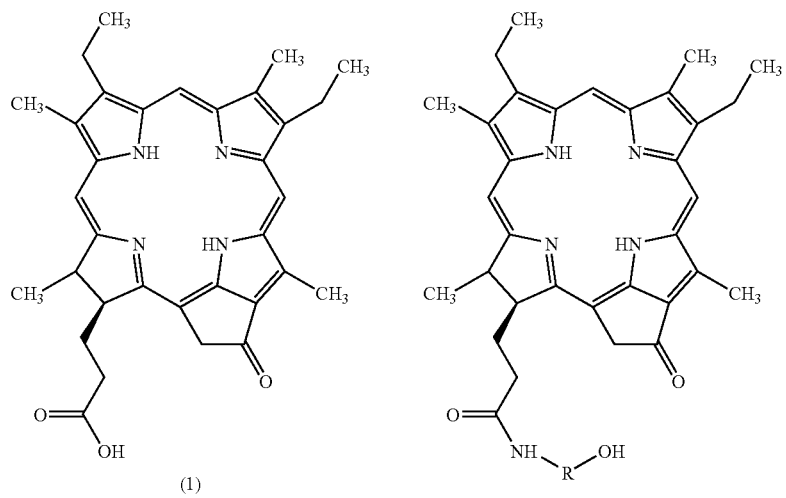

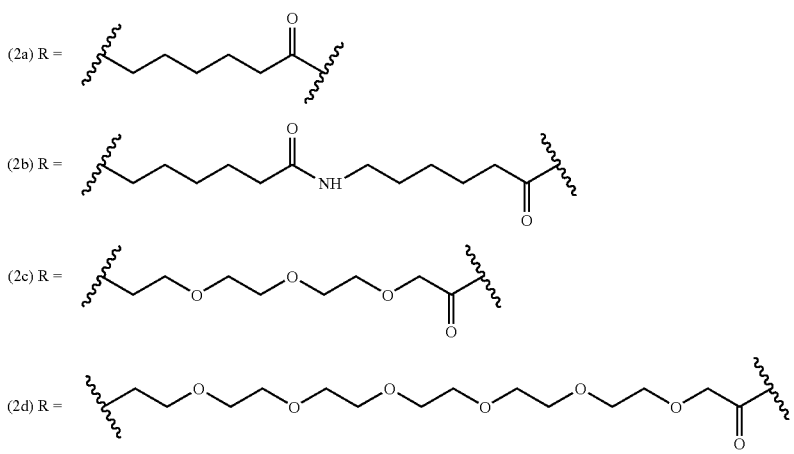

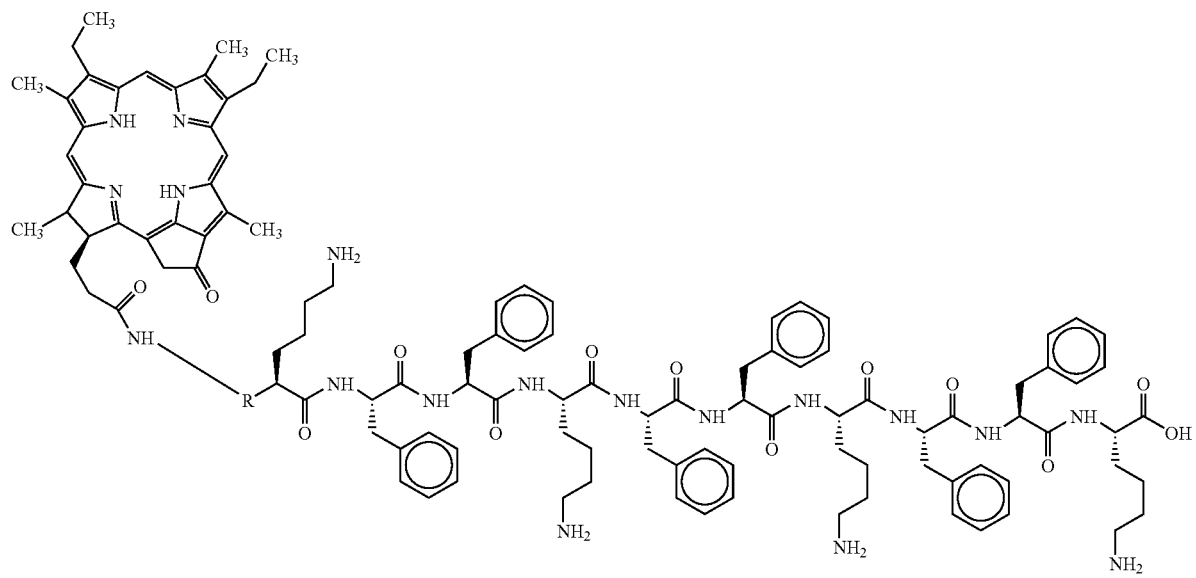

(3a) R = none (3b) R = 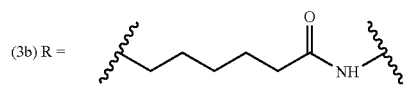

(3c) R = 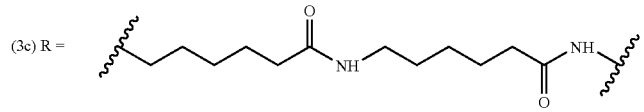

(3d) R = 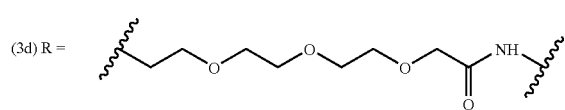

(3e) R = 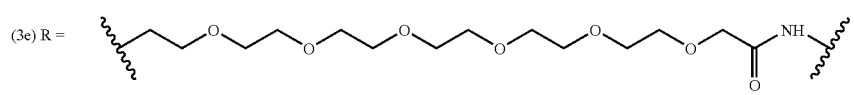

In the preferred embodiment, the antibacterial treatment includes the administration of photosensitizers to an environment containing bacteria and is allowed to incubate for a sufficient period of time thus providing accumulation of the photosensitizer into the bacterial cells. The incubation time varies depending on many factors. In this experiment it is incubated for 30 min before being irradiated with 665 nm laser at 100 J/cm² to initiate photodestruction of bacterial cells. The photosensitizer can be administered either by systemic application, or local injection in the affected area. For infection on or near the skin it can be administered topically.

Figure 2A:
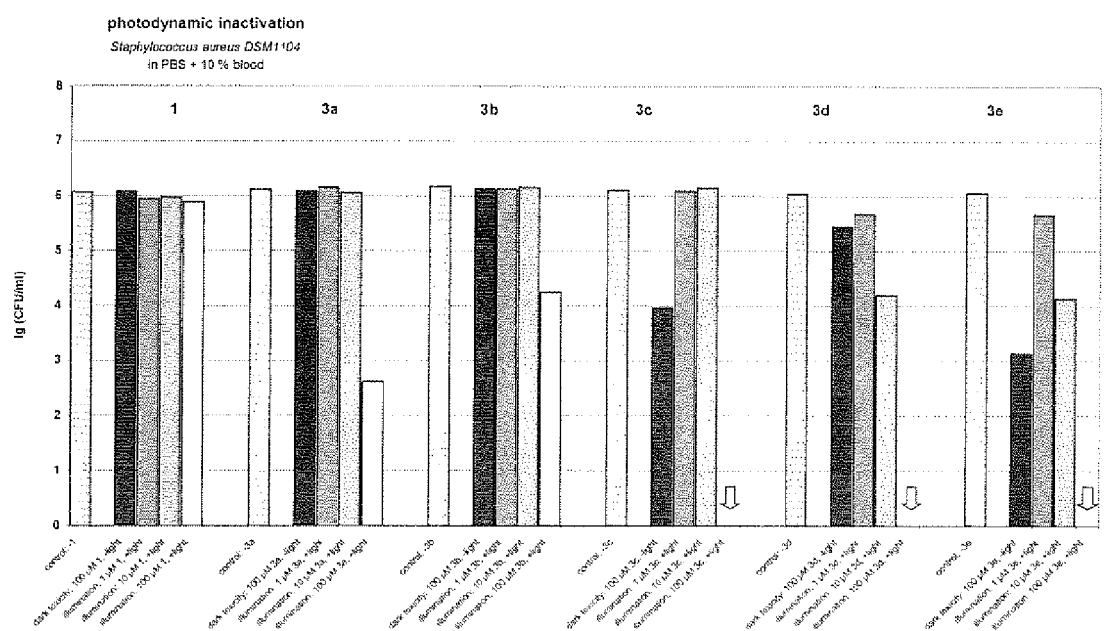
FIG. 2, Graph showing photodynamic inactiviation of *Staphylococcus aureus* DSM1104 (FIG. 2A), *Pseudomonas aeruginosa* DSM1117 (FIG. 2B), and *Escherichia coli* DSM8698 (FIG. 2C) by treatment with compounds 1, 3a, 3b, 3c, 3d and 3e as photosensitizers.
Figure 2B:
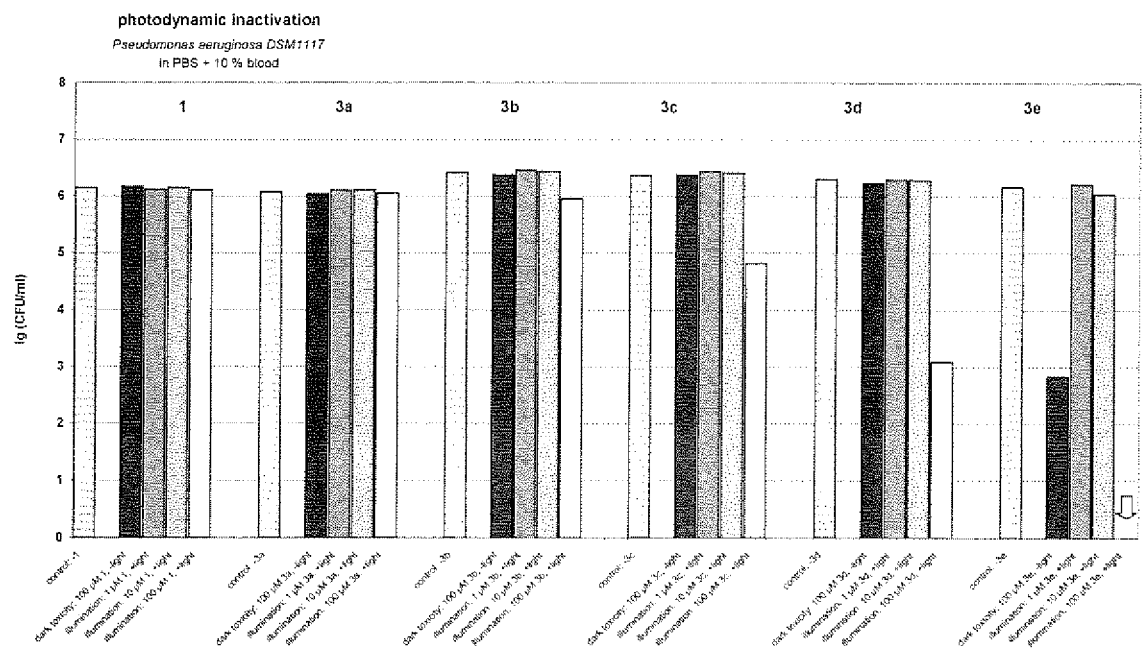
Figure 2C:
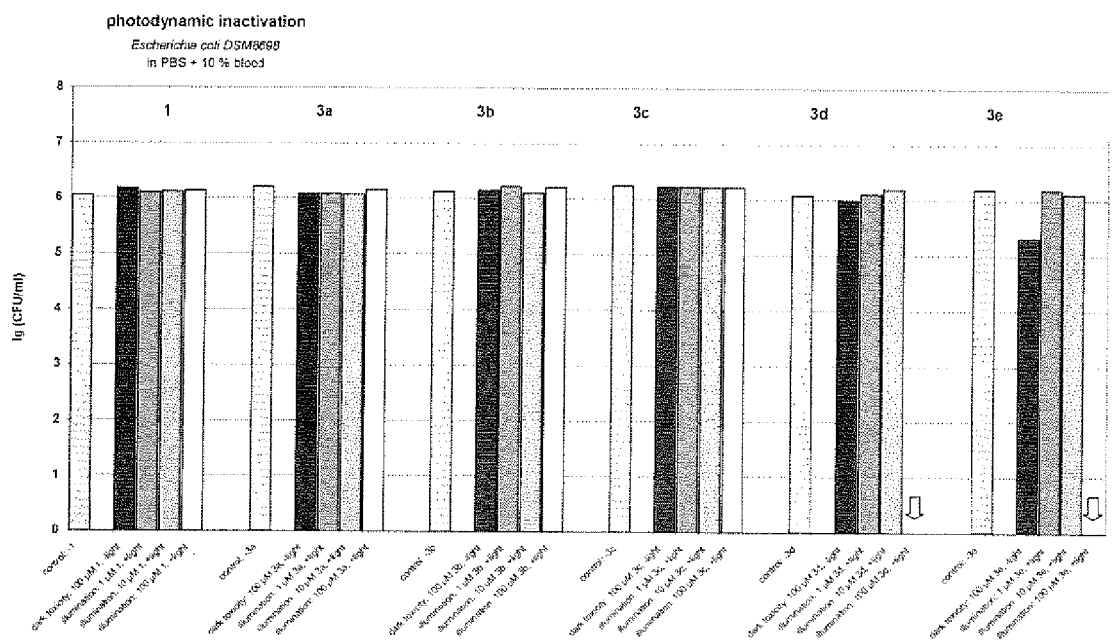

Data on FIG. 2 clearly show that the presence of spacer and its structure is critical for the photodynamic activity of conjugate in the presence of blood. Thus the conjugate without spacer (compound 3a) as well as the conjugates 3b and 3c having hydrophobic aminocapronic acid (7 atoms spacer) and dimeric aminocapronic acid (14 atoms spacer) spacers are not active against Gram-positive and Gram-negative bacteria in the presence of blood. On contrary the conjugates 3d and 3e demonstrate high photodynamic activity in these conditions against both types of bacteria and similarly against fungi including *Candida albicans* (data not shown on FIG. 2).

The present invention is further illustrated by the following examples, but is not limited thereby.

EXAMPLES

The following examples are presented to provide those of ordinary skill in the art with a full and illustrative disclosure and description of how to prepare the conjugates between peptide vector and spacer-armed photosensitizer and are not intended to limit the scope of what the inventors regards as the invention. Efforts have been made to ensure accuracy with respect to numbers used (e.g. amounts, temperature etc.), but some experimental errors and deviations should be accounted for.

Examples 1-4 illustrate preparation of spacer with varying chain length to be used in this invention

Example 1

Preparation of Amide 2c

Typical Procedure

Mesopyropheophorbide-a (1) (237 mg, 0.443 mmol, prepared as described in U.S. Pat. No. 6,777,402) was dissolved in 20 mL of dichloromethane, then 0.3 mL (2.22 mmol. ~5 eq.) of triethylamine was added followed by addition of 0.1 mL (0.576 mmol, 1.3 eq.) of pentafluorophenyl trifluoroacetate. The mixture was stirred at room temperature for 20 min, washed with water, concentrated, and dissolved in a mixture of 2 mL of dichloromethane and 12 mL of dioxane. To this mixture a solution of compound 2 [200 mg (0.965 mmol, 2.17 eq.), product of GlycoSense AG, Jena, Germany] in a mixture of 5 mL of MeOH, 1.2 mL of water and 0.25 mL of 6N KOH was added. The mixture was stirred at room temperature for 30 min, diluted with dichloromethane, then washed with water and 5% sulfuric acid, dried, and concentrated. The residue was purified by flash chromatography on Silica gel. Elution with MeOH-dichloromethane (2→15%) gave 282 mg (88%) of amide 4.

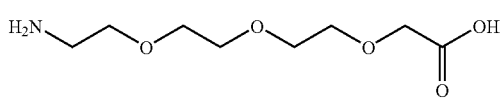

Example 2

Preparation of Amide 2a

Amide 2a was prepared in a 92% yield by, coupling of compound 1 and aminocapronic acid according to the typical procedure as described in the Example 1.

Example 3

Preparation of Amide 2b

Amide 2b was prepared in a 79% yield, by coupling of 2a and aminocapronic acid according to the typical procedure as described in the Example 1.

Example 4

Preparation of Amide 2d

Amide 2d was prepared in an 86% yield by coupling of compound 1 and amino acid 5 (product of GlycoSense AG, Jena, Germany) according to the typical procedure as described in the Example 1.

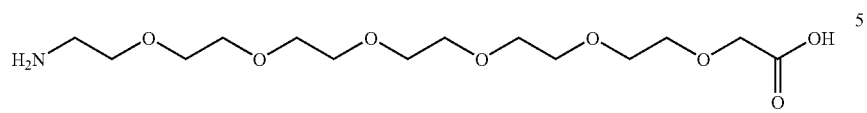 [SMILES: NCCOCCOCCOCCOCCOCCOCC(=O)O]

Example 5 and 6 illustrates the preparation of photosensitizer-spacer-vector conjugate for one of the example compound.

Example 5

Preparation of Peptide-Photosensitizer Conjugate 3d

Typical Procedure, Homo-Phase Conditions

Acid derivative 2c (40 mg, 0.055 mmol, 2.97 eq.) was dissolved in 5 mL of dichloromethane, then 0.1 mL (excess) of triethylamine was added followed by addition of 0.05 mL (excess) of pentafluorophenyl trifluoroacetate. The mixture was stirred at room temperature for 20 min, washed with water, concentrated, and dissolved in 2 mL of pyridine. This mixture was added to a solution of decapeptide 6 [50 mg, purity of 67% (0.0185 mmol), product of Biosyntan GmbH, Berlin, Germany] in a mixture of 2 mL of pyridine and 0.04 mL of 40% aqueous solution of tetra-n-butyl ammonium hydroxide. The mixture was stirred at room temperature for 2 hrs, diluted with dichloromethane, then washed with 5% sulfuric acid, dried, and concentrated. The residue was purified on Silica gel and gradient elution with MeOH—$CH_2Cl_2$ (0→15%) to give protected conjugate (40 mg). This derivative was treated with 2 mL of HCl conc. at room temperature for 25 min, evaporated to dryness, and purified via MPLC on Lobar-RP18 (size B) column and gradient elution with acetonitrile-water (+0.1% TFA) (0→50%) to give 29 mg (56%) of pure conjugate 3d.

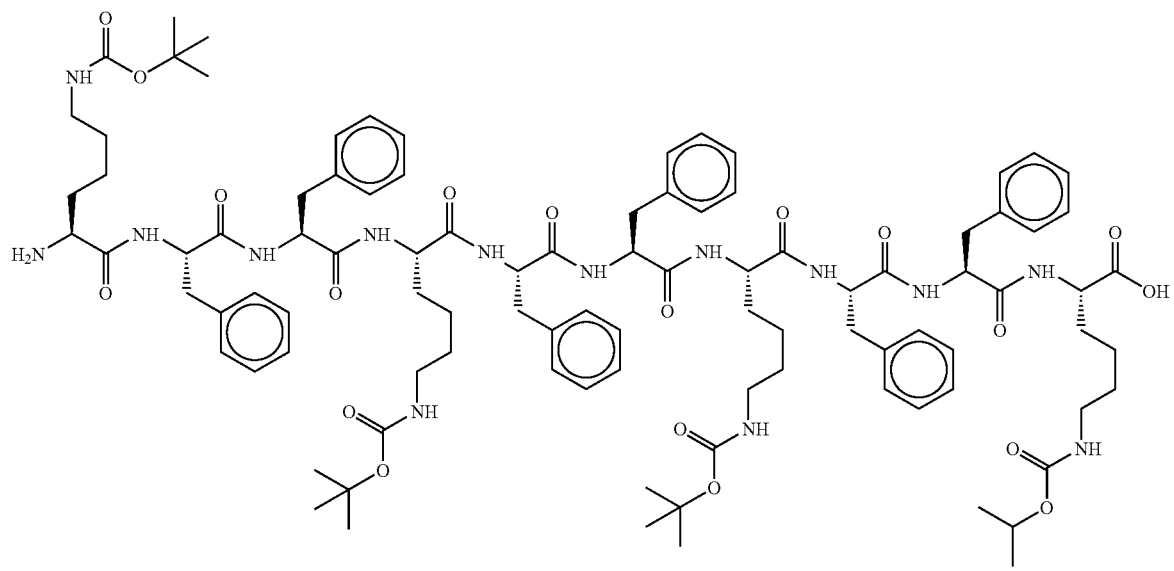

6

Example 6

Preparation of Peptide-Photosensitizer Conjugate 3d

Typical Procedure, Solid-Phase Conditions

Conventional procedure of solid-phase peptide synthesis comprising first assembling selectively N-blocked decapeptide backbone (corresponds to the peptide sequence ID No. 1: KFFKFFKFFK, like in the block 6) and subsequent adding of spacer conjugated meso pyropheophorbide-o moiety by treatment with acid derivative 2c in the presence of standard condensation reagents and subsequent removal of the corresponding conjugates from the resin were used to produce crude product 3d. Its further chromatography purification was performed as described above in Example 5 to give pure 3d.

Example 7

Photodynamic Inactivation of Bacterial Cell Suspension Using Photosensitizers 3a-e The organisms used in our studies were three members of the microflora of wounds: *Staphylococcus aureus* DSM1104, Gram-positive; *Escherichia coli* DSM8698, Gram-negative; *Pseudomonas aeruginosa* DSM1117, Gram-negative.

Several studies have demonstrated that Gram-positive bacteria (e.g. *Staphylococcus aureus*) are particularly susceptible to photodynamic inactivation whereas Gram-negative bacteria (e.g. *Escherichia coli, Pseudomonas aeruginosa*) are significantly more resistant to many commonly used photosensitizers. Moreover, it has been found that both Gram-positive and Gram-negative bacterial cells in complex media (e.g. blood, plasma, blood serum, saliva) are much less susceptible to standard photosensitizer conjugates.

Cultured cells are suspended in sterile phosphate-buffered saline (PBS) or sterile PBS supplemented with 10% sterile horse blood serum, 10% human plasma or 10% human blood respectively. The final OD (Optical Density) at 600 nm, 1 cm in all cases was 0.03. The bacterial suspensions are placed into sterile black well plates with clear bottoms. Concentrations of photosensitizer 1 and photosensitizer conjugate 3a (without spacer), and 3b, 3c, 3d, 3e (with spacer) used in the study is as follows: 100 µM, 1 µM, 10 µM, and 100 µM.

After incubation the samples are exposed to laser light of 665 nm, power set to 0.5 W, and irradiation time of 85 s. With the irradiation time, the resulting energy fluency was about 100 J/cm$^2$. Control plates contained no photosensitizer and are not exposed to laser light. The control samples for dark toxicity are only exposed to photosensitizer (end concentration of 100 mM) without any illumination.

After irradiation the samples are removed and suspended again in the culture media. The numbers of colony-forming units (CFU/ml) are enumerated after adequate incubation.

The result of the above study is shown in the FIG. 2 wherein it is clearly shown that the presence of spacer and its structure is critical for the photodynamic therapy in the presence of blood or other body fluids. It can be clearly seen from FIG. 2 that photosensitizer compound 1, conjugate compound 3a (without spacer), conjugate 3b (with 7 atom hydrophobic aminocarpronic acid spacers), and conjugate 3c (with 14 atom hydrophobic aminocarpronic acid spacers) are not active against Gram-positive and Gram-negative bacteria in the presence of blood. Conjugates 3d and 3e with spacer demonstrates high photodynamic activity against both Gram-positive and Gram-negative bacteria in presence of blood.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A molecular conjugate comprising a mesopyropheophorbide-a and a targeting peptide, wherein said targeting peptide is SEQ ID NO: 1, and wherein the mesopyropheophorbide-a and targeting peptide are connected by a hydrophilic spacer comprising up to 45 atoms, at least three ethylene glycol units, an amino end cap and a carboxyl end cap.

2. The molecular conjugate of claim 1, wherein said backbone spacer has a structure selected from the group consisting of:

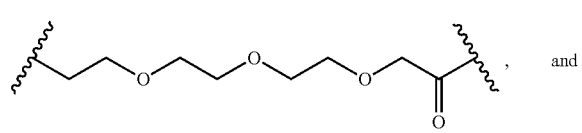, and

C

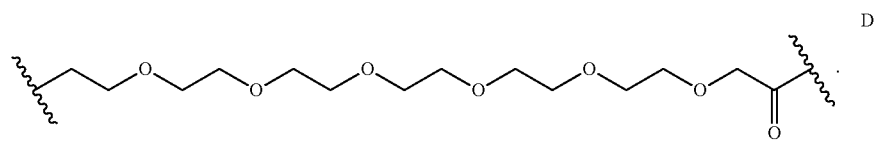.

D

3. The molecular conjugate of claim 1, wherein said spacer is no longer than 21 atoms.

4. The molecular conjugate of claim 2, wherein said spacer is

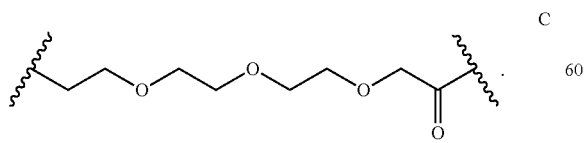.

C

5. The molecular conjugate of claim 2, wherein said spacer is

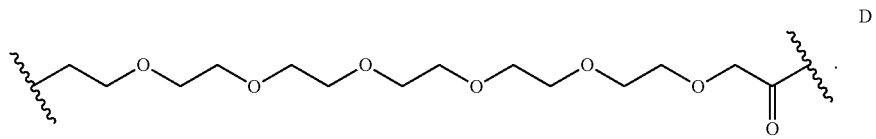 [SMILES: *CCOCCOCCOCCOCCOCCOCC(*)=O]

6. A method of inactivating or reducing microorganisms in at least one of blood, serum, plasma or saliva comprising the steps of:
   selecting a molecular conjugate, according to claim 1, with a peptide component targeting said microorganisms to be inactivated or reduced;
   introducing said molecular conjugate to said at least one of blood, serum, plasma or saliva;
   allowing time for said molecular conjugate to accumulate in said targeted microorganisms; and,
   irradiating said targeted microorganisms with an appropriate wavelength to activate said molecular conjugate to destroy said targeted microorganisms.

7. The method of claim 6, wherein said targeted microorganisms are Gram-negative or Gram-positive microorganisms.

* * * * *